United States Patent [19]
Adams

[11] Patent Number: 5,369,351
[45] Date of Patent: Nov. 29, 1994

[54] HIGH VOLTAGE CHARGE STORAGE ARRAY FOR AN IMPANTABLE DEFIBRILLATOR

[75] Inventor: Theodore P. Adams, Edina, Minn.

[73] Assignee: Angeion Corporation, Plymouth, Minn.

[21] Appl. No.: 835,837

[22] Filed: Feb. 18, 1992

[51] Int. Cl.⁵ .......................... H02J 7/00; A61N 1/36
[52] U.S. Cl. ......................................... 320/7; 320/13; 320/14; 320/16
[58] Field of Search ..................... 320/7, 8, 16, 13, 14; 128/419 PS

[56] References Cited

U.S. PATENT DOCUMENTS

| | | | |
|---|---|---|---|
| 3,871,383 | 3/1975 | Lee | 320/13 X |
| 4,814,631 | 3/1989 | Jackson | 320/7 X |
| 5,154,989 | 10/1992 | Howard et al. | 429/160 |

Primary Examiner—R. J. Hickey
Attorney, Agent, or Firm—Patterson & Keough

[57] ABSTRACT

An electrochemical charge-storage system for defibrillator energy delivery where a plurality of switched battery cells with high energy storage capacity are incorporated for delivering an electrical charge within an implanted defibrillator system. Alternative embodiments include circuitry for battery replacement switching of a faulty battery.

13 Claims, 5 Drawing Sheets

HIGH VOLTAGE CHARGE STORAGE ARRAY FOR AN IMPANTABLE DEFIBRILLATOR

BACKGROUND OF THE INVENTION

1. Field of the Invention

The present invention pertains to a the power supply for medically implanted device, and more particularly, pertains to a battery-discharge method for powering an implanted defibrillator device.

2. Description of the Prior Art

In defibrillators available today, both implantable and external, energy is delivered to the electrodes by the discharge of capacitors. Prior to the shock initiation, a converter circuit is typically used to charge a high-energy capacitor to a high voltage ranging from several hundred volts in an implantable device to several thousand volts in an external device. Because capacitors are relatively space-inefficient, as energy-storage devices characteristically are, 2 joules/cc for an aluminum electrolytic capacitor, the output capacitors are the largest components in a defibrillator. This is not a major problem in external defibrillators, but it is a critical problem in implantable defibrillator systems. Many attempts to develop higher energy density capacitors have been made in the last five years with the objective of possibly doubling the energy density of aluminum electrolytic capacitors without success. The present invention discloses a method of storing and delivering the same energy to the heart from a device with 2 to 3 orders of magnitude more energy density than conventional capacitors.

Prior art devices have failed to provide a means that is compact for storage of an electrical charge for an implanted defibrillator device. Prior art systems employed capacitors that were large and bulky and that took up an inordinate amount of space in the implanted device.

The present invention overcomes the disadvantages of the prior art devices by providing a electrochemical charge-storage system having a plurality of switched cells to provide an electrical charge for an implanted defibrillator system.

The present invention adapts, for implantable medical-electronic systems, a concept employed in other contexts and technologies. A prior art technique for achieving high voltages that predates even solid-state electronics employs an array of capacitors. By charging them in parallel from a relatively low-voltage supply, and then connecting the capacitors in series by means of a switching network, one creates the condition for a high-voltage capacitor discharge. The present invention makes a major improvement on this technique.

SUMMARY OF THE INVENTION

The general purpose of the present invention is to provide a more compact medically implanted device, and more particularly to provide a battery-discharge method for powering an implanted defibrillator device.

In the present invention, the capacitor of the prior art devices is replaced by a stack of rechargeable batteries that are charged from the primary battery in parallel and discharged through the heart in series. There are available certain lithium battery systems having a polymer electrolyte that can be manufactured in foil sheets of thickness less than 0,005". An example is the Li/V-$_6$O$_{13}$ cell made by Mead Corporation in Denmark. These cells have an energy-storage capacity of over 1000 times that of capacitors of equivalent volume. Thus, the volume required to store the energy for one output pulse is significantly less than that of a capacitor. Two hundred small capacity cells of approximately three volts each would produce a voltage equivalent to that typically used in implantable defibrillators. If the cells are made of sufficient size, enough energy can be stored to produce more than one shock of approximately 20–30 joules each on a single charge. A further space saving accrues from not needing the inverter circuitry necessary for charging an output capacitor. Switching circuitry is also provided to switch a faults battery from the series discharging circuit and to, at the same time, switch in a spare or reserve replacement battery into the series discharge circuit.

According to one embodiment of the present invention, there is provided a electrochemical charge-storage system for defibrillation energy delivery, where a large plurality of physically small cells having a high energy density are charged in parallel from a main battery and switched by control electronics into series to deliver a charge to the heart.

In the most fundamental terms, the advantage in the present invention is this: A capacitor is a physical structure that functions because of the attraction of unlike charges, and converts this attraction into storage. It provides two conductors spaced apart by an insulator. Although very small dimensions (especially thickness dimensions) have been achieved in the capacitor art, they are still macroscopic on an atomic scale. In electrochemical storage, on the other hand, storage occurs on an atomic scale. For this reason, the energy density of storage achievable in the "battery" art greatly exceeds that of the capacitor.

The essence of the present invention is a new two-way combination and a new three-way combination. The first element is a modern and solid-state version of the kind of switching network that has long been used to convert an array of charged capacitors into a series "string" for the purpose of achieving a high-voltage discharge. To create the new two-way combination, such a network is employed with high-energy-density electrochemical cells for achieving a high-voltage discharge. While the aim here is primarily to power an implantable defibrillator-cardioverter with a more space-efficient source, it will be evident that the innovative combination just described has much broader relevance.

In the new three-way combination, one chooses the electrochemical cells to be rechargeable devices, such as the lithium-vanadium-oxide cells now available from Denmark, and one adds as the third element a primary power source for recharging. In the preferred embodiment at present, this source is a comparatively low-voltage battery. But it will be evident further that variations can be introduced without departing from the scope and spirit of the invention. For example, the switching can be reversed. Then in principle, an extremely high-voltage source, such as shoes on a nylon carpet, can be exploited to charge the cells in series in order to deliver significant current when the cells are switched to a parallel configuration.

The miniscule volume of the cell array of this invention opens the door to further innovation. The failure of one cell could disable the entry circuit and require surgical intervention to replace the unit. To avoid the need to replace the unit when a cell fails, a spare block of cells can be included as described in the alternative embodiments. Take, for example, the array of two hundred 3-volt cells cited above. These could be configured in four 50-cell blocks that would each deliver 150 volts when in series, for a total voltage of 600 volts. Providing a fifth 50-cell block would then through straightforward switching permit the delivery of a 750-volt pulse, if desired. Further, a reliability improvement can be achieved by providing test-and-reconfigure circuitry that would use the alternate block to replace a block that became defective. This technique has been used for decades in the microelectronic-memory art, but primarily for yield improvement. The lesson learned there has been that the replacement block should be a relatively large fraction of the overall array, as in the example just given.

One significant aspect and feature of the present invention is a battery of high-energy-density cells.

Another significant aspect and feature of the present invention is the reduction in size of an implanted system through the elimination of large capacitors.

Another significant aspect and feature of the present invention is a switching arrangement to configure the high-energy-density cells in parallel or series.

Still another significant aspect and feature of the present invention is the recharging of high-energy-density electrochemical cells from a low-voltage primary battery.

Yet another significant aspect and feature of the present invention is accomplishing with efficient electrochemical cells what has long been practiced in other technologies with less efficient capacitors.

Another significant aspect and feature of the present invention is a defibrillator and cardioverter small enough for pectoral implantation.

Still another significant aspect and feature of the present invention is maintaining cells fully charged in the standby condition, and ready for immediate discharge via a switching network.

Yet another significant aspect and feature of the present invention is low-to-high voltage conversion.

Another significant aspect and feature of the present invention is high-to-low voltage conversion.

Yet another significant aspect and feature of the present invention is provision of at least one extra block of cells for voltage flexibility and reliability improvement.

Having thus described one embodiment of the present invention, it is the principal object hereof to provide an electrochemical charge-storage system for defibrillation energy delivery.

A further object of the present invention is to achieve a defibrillator and cardioverter small enough for pectoral implantation.

A still further object of the present invention is to combine an array of high-energy-density electrochemical cells and a switching network that is able to configure them in series or parallel.

Still another object of the present invention is charge maintenance in an array of high-energy-density electrochemical cells by means of a primary battery.

A further object of the present invention is replacing capacitor arrays of the past with more efficient electrochemical cells.

A still further object of the present invention is to provide cell redundancy for reliability while maintaining acceptable power-supply volume.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENT

Figure 1:
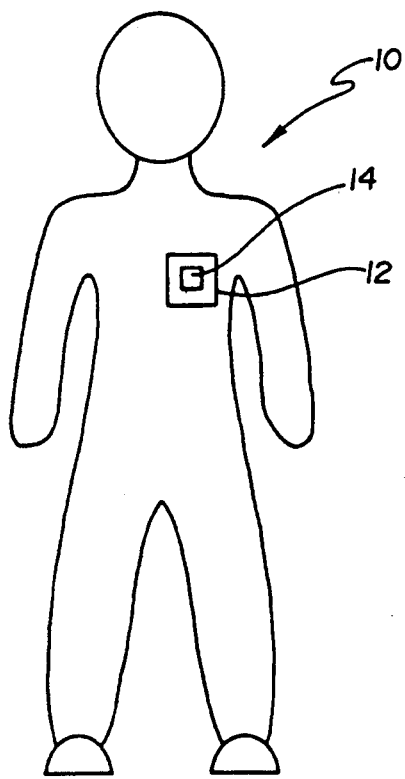
FIG. 1 illustrates an implanted defibrillator system in a person.

FIG. 1 illustrates a person 10 fitted with an implanted system 12 that incorporates an electrochemical charge-storage system 14 for defibrillation energy delivery, herein also known as a charge-storage system.

Figure 2:
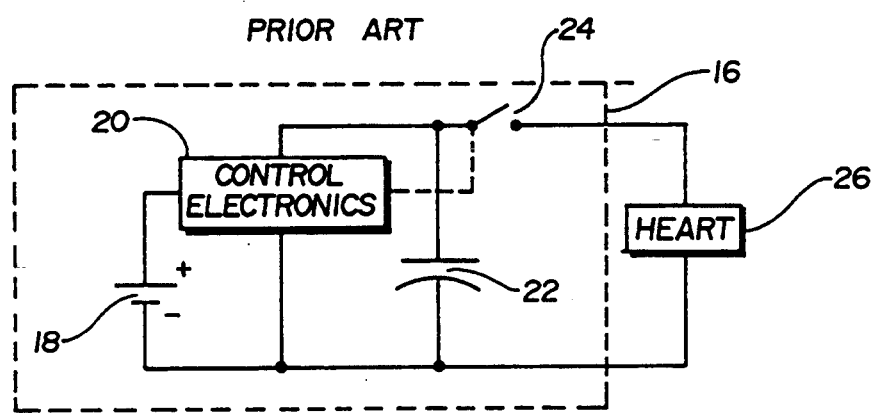
FIG. 2 illustrates a prior art charge-storage system for an implanted defibrillator device.

FIG. 2 illustrates a prior art charge-storing system 16 for an implanted defibrillator having a battery 18, control electronics 20, an output capacitor 22, and a switch 24 connected to a heart 26.

Figure 3:
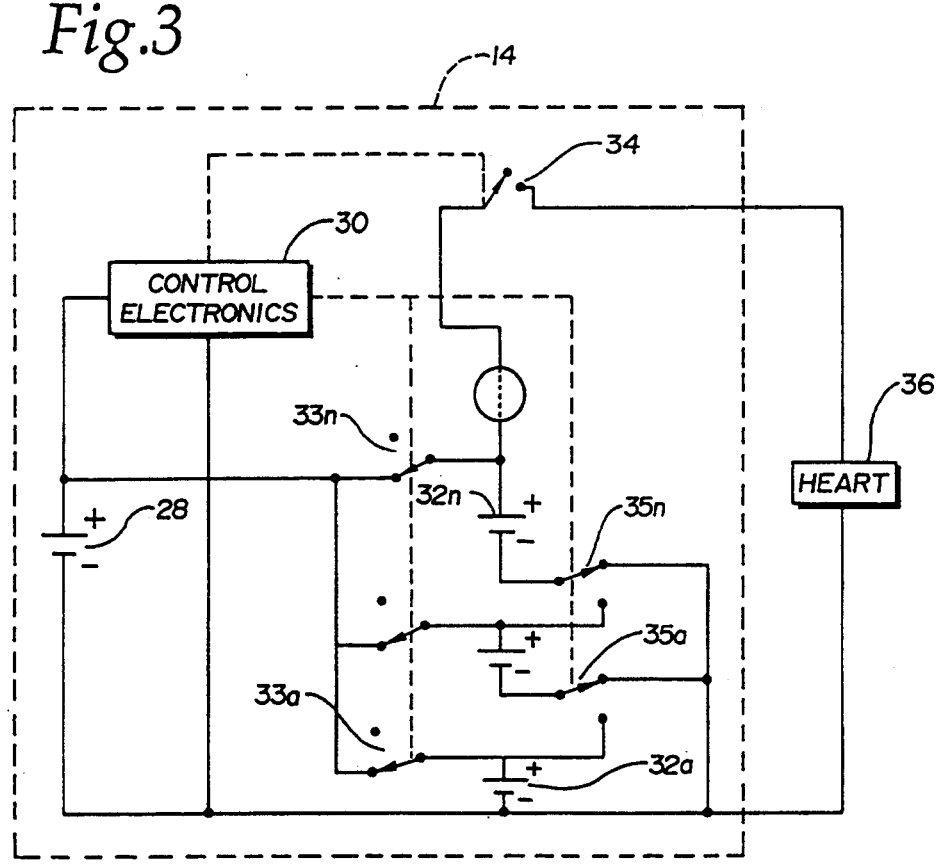
FIG. 3 illustrates an electrochemical charge system, the present invention, for defibrillation energy delivery in the charge mode.
Figure 4:
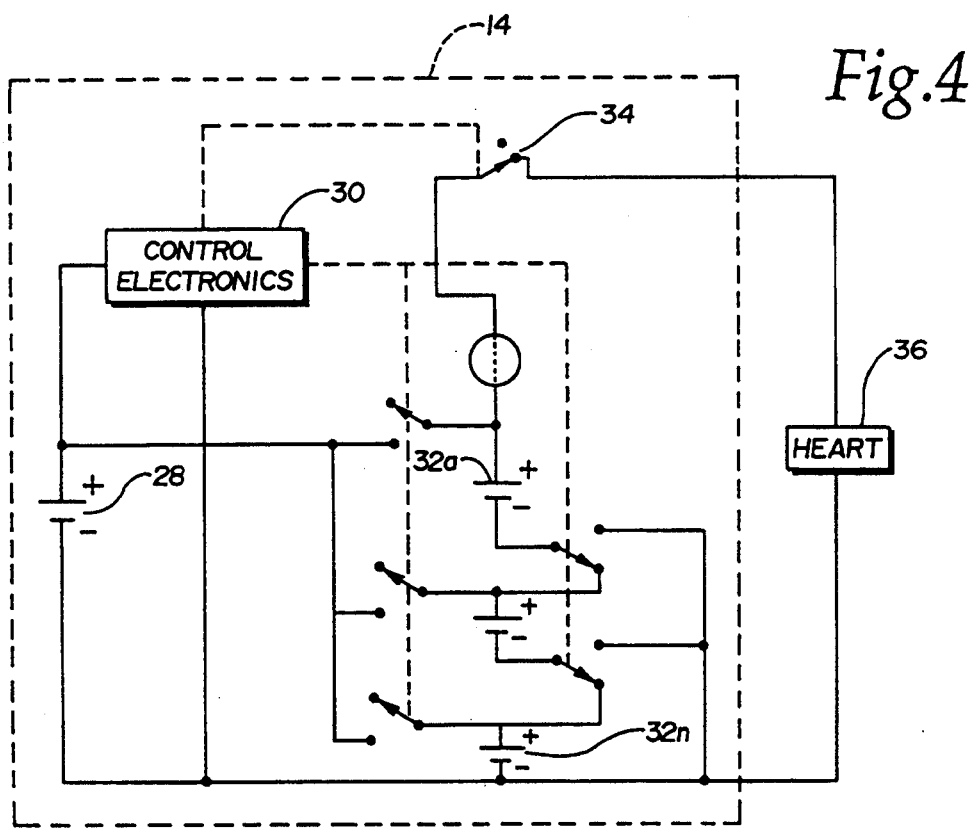
FIG. 4 illustrates the electrochemical charge system in the series discharge mode.

FIG. 3 illustrates the present invention, a charge storage system 14 including a primary battery 28, control electronics 30, a plurality of high capacity battery cells 32a–32n, such as Li/V$_6$O$_{13}$ cells, and a switch 34 connected to a heart 36. Switches 33a–33n and 35a–35n connect to the battery cells 32a–32n to switch the battery cells 32a–32n to parallel the batteries 32a–32n with the primary battery 28 for charging purposes. In operation the cells 32a–32n are charged by the primary battery 28 and maintained at full charge until fibrillation is detected. The low self-discharge rate of these types of cells 32a–32n allows them to be kept fully charged at all times. When fibrillation is detected, the control electronics 30 first switches the cells 32a–32n into a series configuration by repositioning switches 33a–33n and 35a–35n and then closes the switch 34 connecting them to the heart 36 for discharge as illustrated in FIG. 4. A timing circuit in the control electronics 30 then opens the switch 34 after sufficient energy has been delivered to the heart 36. A further improvement can include switching means to reverse the connections between the heart 36 and batteries 32a–32n during the pulse to create a biphasic waveform.

FIG. 4 illustrates a schematic drawing of the present invention where the batteries 32a–32n have been switched to a series configuration and connected via switch 34 to the heart 36 for delivery of a charge to the heart 36 where all numerals correspond to those elements previously described.

DESCRIPTION OF THE ALTERNATIVE EMBODIMENTS

Figure 5:
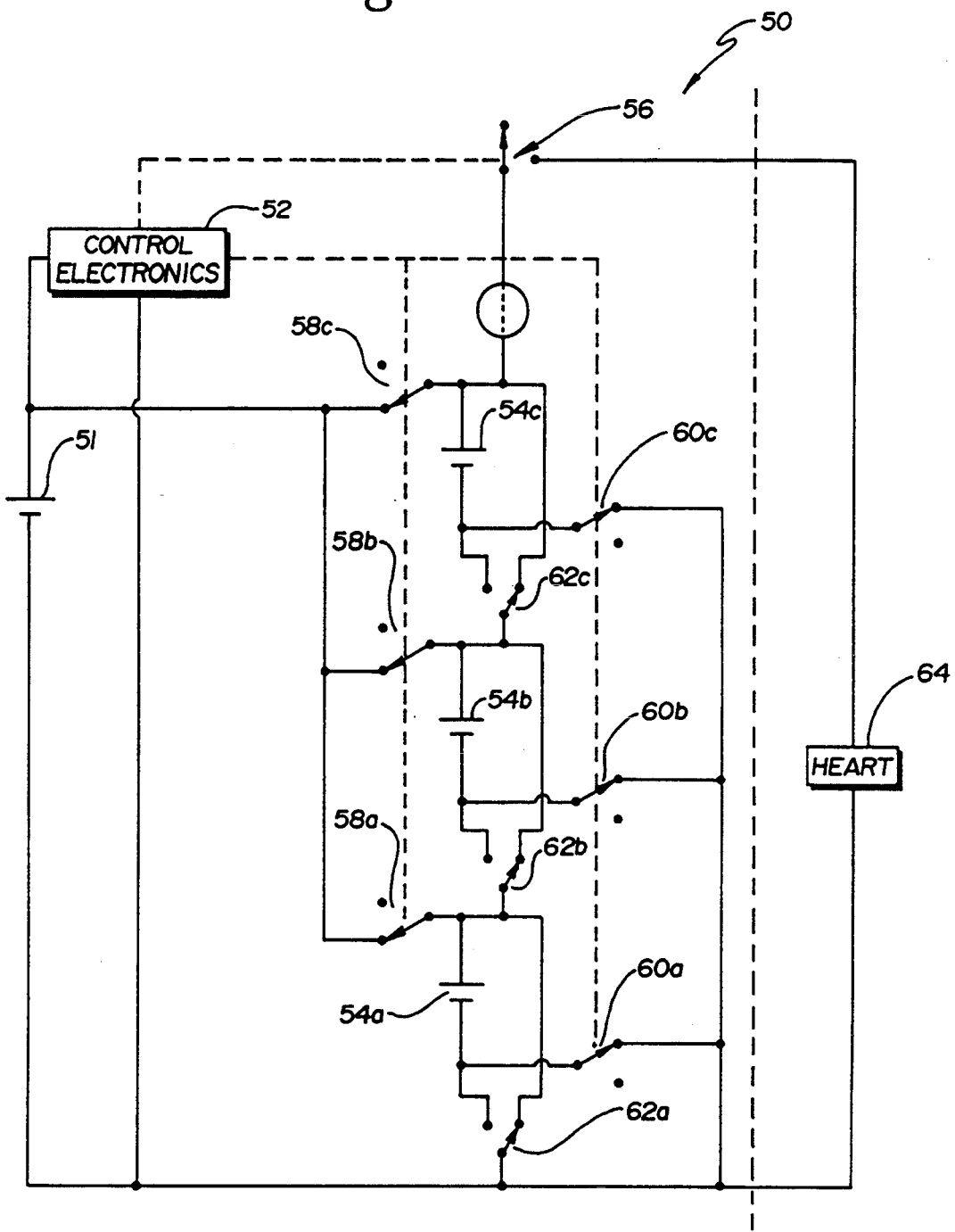
FIG. 5, an alternative embodiment, illustrates circuity for faulty battery replacement.
Figure 6:
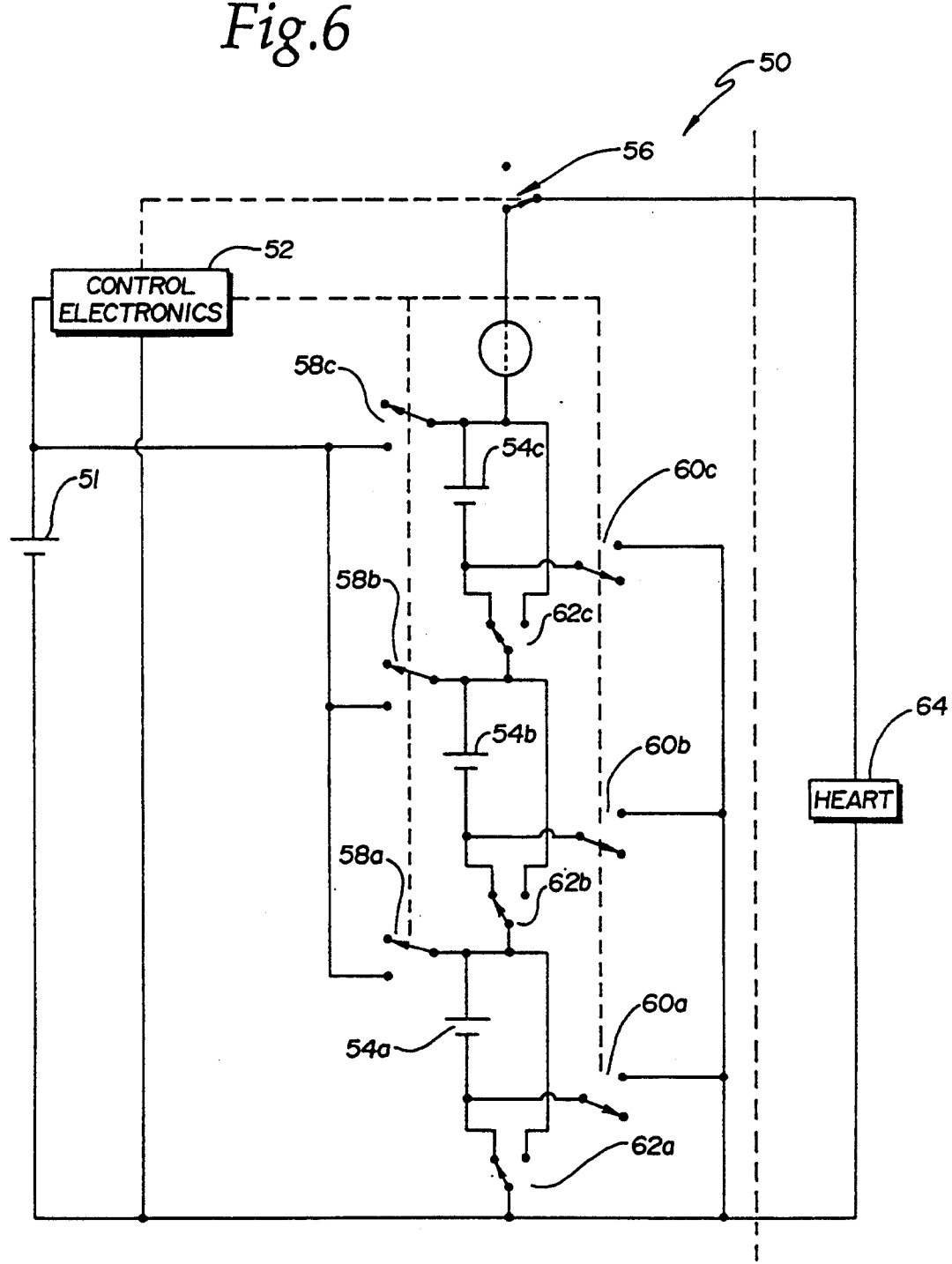
FIG. 6, an alternative embodiment, illustrates the circuitry of FIG. 5 in the discharge mode.
Figure 7:
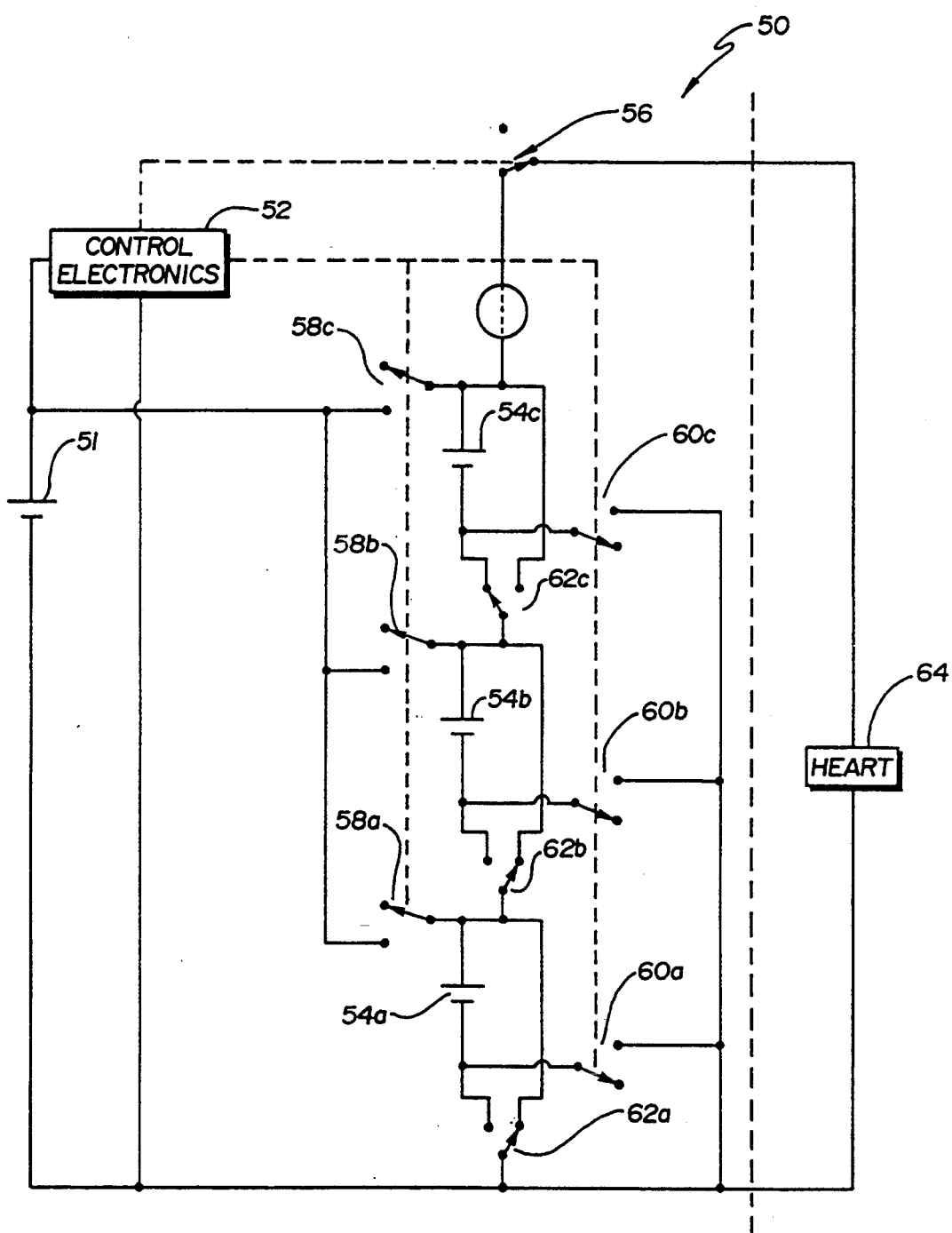
FIG. 7, an alternative embodiment, illustrates the circuitry of FIG. 5 in the discharge mode where a reserve battery cell has replaced a faulty battery cell.

FIGS. 5, 6 and 7, alternative embodiments, are each circuits based upon the circuitry of and principals of FIGS. 3 and 4 having the same basic components plus additional switching circuits. An automatic battery substitution feature is included in these embodiments. Members of the electrochemical charge storage system for defibrillation energy 50 include a battery 51, control electronics 52, a plurality of batteries, including batteries 54a, 54b and 54c, a switch 56, a plurality of switches, including switches 58a, 58b and 58c, a plurality of switches, including switches 60a, 60b and 60c, and a plurality of switches, including switches 62a, 62b and 62c connected to a heart 64.

FIG. 5 illustrates the circuit 50 where the switches 62a, 62b and 62c are in parallel with and being charged by the battery 51 by the positioning of switches 58a–58c and 60a–60c where all numerals correspond to those elements previously described.

FIG. 6 illustrates the discharge mode where the active batteries are aligned in series for delivery of a defibrillation shock to the heart while a reserve battery is not used where all numerals correspond to those elements previously described. In this illustration the control electronics 53 have sensed that all the batteries 54b and 54c are in proper working condition. Switches 58a–58c, 60a–60c, and 62a–62c are positioned for series operation of the batteries 54b–54c while a good battery 54a is kept in reserve and not at this moment used in the series battery circuit. Switch 56 is also positioned to deliver a charge from the series batteries to the heart 64.

FIG. 7 illustrates the discharge mode where a faulty battery is switched out and replaced by a reserve battery where all numerals correspond to those elements previously described. In this illustration the control electronics 53 have sensed that battery 54b is faulty. Switches 58a–58c, 60a–60c, and 62a–62c are positioned for series operation of the normal batteries, such as battery 54c, but the faulty battery 54b is switched out of the series battery circuit and the reserve or good battery 54a is switched into series with the good battery bank beginning with battery 54c. Switch 56 is positioned for delivery of a charge to the heart 64.

Various modifications can be made to the present invention without departing from the apparent scope hereof.

I claim:

1. A high voltage charge storage array for an implantable device comprising:
   an array of at least about fifty low voltage battery cells; and
   switching means electrically connected to each battery cell for selectively discharging the battery cells in series to produce a high voltage output to be delivered by the implantable device that is at least an order of magnitude greater than an output voltage of the low voltage battery cells.

2. The charge storage array of claim 1 wherein the implantable device is an implantable defibrillator and the high voltage output is a countershock of at least about 150 volts.

3. The charge storage array of claim 2 wherein each battery cells has a higher energy density than a capacitive charge storage device.

4. The charge storage array of claim 3 wherein each battery cell is a lithium-vanadium-oxide cell.

5. A high voltage charge system for an implantable device comprising:
   an array of at least about fifty low voltage rechargeable battery cells;
   switching means electrically connected to each battery cell for selectively discharging the battery cells in series to produce a high voltage output to be delivered by the implantable device that is at least an order of magnitude greater than an output voltage of the low voltage battery cells and for selectively configuring the array of battery cells in parallel for recharging; and
   primary battery means electrically connected to the switching means for supplying electrical energy at a low voltage to the array of battery cells in parallel to charge the battery cells.

6. The system of claim 5 wherein the low voltage is less than about 6 volts.

7. The charge storage array of claim 1 wherein the battery cells are arranged into two or more groups of cells and the switch means is further provided with means for selectively switching as a group one or more of the groups of cells into and out of active use in producing the high voltage countershock.

8. A high voltage charge storage array for an implantable device comprising:
   an array of at least about fifty low voltage rechargeable battery cells;
   primary battery means for supplying electrical energy at a low voltage to the array of battery cells to charge the battery cells.
   switching means electrically connected to the primary battery means and to each battery cell for selectively charging the battery cells in parallel at the low voltage and selectively discharging the battery cells in series to produce a high voltage output to be delivered by the implantable device that is at least an order of magnitude greater than the low voltage.

9. The charge storage array of claim 8 wherein the implantable device is an implantable defibrillator and the high voltage output is a countershock of at least about 150 volts.

10. The charge storage array of claim 9 wherein each battery cells has a higher energy density than a capacitive charge storage device.

11. The charge storage array of claim 10 wherein each battery cell is lithium-vanadium-oxide cell.

12. The charge storage array of claim 8 wherein the low voltage is less than about 6 volts.

13. The charge storage array of claim 8 wherein the battery cells are arranged into two or more groups of cells and the switch means is further provided with means for selectively switching as a group one or more of the groups of cells into and out of active use in producing the high voltage countershock.

* * * * *